United States Patent [19]

Li

[11] 4,317,770

[45] Mar. 2, 1982

[54] D-AMINO ACID ANALOGS OF BETA-ENDORPHIN

[75] Inventor: Choh Hao Li, Berkeley, Calif.

[73] Assignee: Hoffmann-La Roche Inc., Nutley, N.J.

[21] Appl. No.: 776,569

[22] Filed: Mar. 11, 1977

[51] Int. Cl.³ ............................................ C07C 103/52
[52] U.S. Cl. ............................................ 260/112.5 E
[58] Field of Search ................. 260/112.5 R, 112.5 E

[56] References Cited

U.S. PATENT DOCUMENTS 4,038,222   7/1977   Li ................................. 260/112.5 R

OTHER PUBLICATIONS

G. Ungar, et al., Opiates and Endogenous Opioids Peptides 1976 pp. 121–128.

D. H. Coy, et al., Biochem. and Biophys. Res. Commun. 73, 1976, pp. 632–638.

*Primary Examiner*—Delbert R. Phillips
*Attorney, Agent, or Firm*—Jon S. Saxe; Bernard S. Leon; George M. Gould

[57] ABSTRACT

D-amino acid analogs in positions 1,2,4 and 5 of β-endorphin are synthesized by solid phase techniques. These compounds and, particularly [D-Ala$^2$]-β-endorphin, exhibit opiate agonist and analgesic activity.

3 Claims, No Drawings

D-AMINO ACID ANALOGS OF BETA-ENDORPHIN

BACKGROUND OF THE INVENTION

The discoveries of endogenous morphine-like peptides have generated intense interest in their structure-activity relationships. All correspond to portions of the structure of β-lipotropin and possess biological activity to varying degress in in vitro test systems. In contrast, the in vivo analgesic activity of enkephalin injected intracranially appears to be of short duration, while that of β-endorphin is long lasting. Thus far only β-endorphin displays in vivo analgesic activity when injected into the peripheral system. One approach toward understanding the properties of β-endorphin which make it similar to, yet dissimilar from, all the other opioid peptides is through total synthesis of its analogs. The syntheses of camel and human β-endorphins in good yields established conditions which provide facile access to these compounds. Reports on the enzymatic cleavage of the Tyr-Gly bond in enkephalin which can account for the transiency of its analgesic activity led to the development of the analogs [D-Ala$^2$]-enkephalin (Hambrook et al., Nature (Lond.) 258, 577 (1976) and its corresponding amide (Pert et al., Science 194, 330 (1976) which exhibit long-lasting analgesia when injected centrally.

DESCRIPTION OF THE INVENTION

The present invention relates to novel D-amino acid analogs of β-endorphin which have opiate agonist and analgesic activity. More particularly, the present invention relates to analogs of β-endorphin wherein a D-amino acid is substituted for one of the L amino acids present in the enkephalin i.e., positions 1-5, portion of the molecule. Preferably, substitution of the D-amino acid is carried out in positions 1, 2, 4 and 5, most preferably in the 2-position. Thus [D-Ala$^2$]-β-endorphin is a most preferred compound.

As used herein the term β-endorphin is meant to include the various sequences which result from species variability. Thus β-endorphin will include, for example, β-endorphin having a sequence derived from human ($β_h$-endorphin), camel ($β_c$-endorphin) or porcine ($β_p$-endorphin) sources. The parent compounds have exhibited essentially equivalent biological activity.

The analogs of β-endorphin were synthesized by the solid-phase method using the same tactics as for the syntheses of $β_c$- and $β_h$-endorphins. Briefly, these consisted of esterifying Boc-glutamine to brominated styrene-1% divinylbenzene polymer by the Loffet (Int. J. Protein Res. 3, 297 (1971)) method to give a more stable ester linkage. N$^α$-deprotection was effected with 50% trifluoroacetic acid in dichloromethane and couplings by use of symmetrical anhydrides performed with dicyclohexylcarbodiimide. The last stage of coupling was conducted in 20% 2,2,2-trifluoroethanol in dichloromethane to enhance coupling efficiencies. The final Boc group was removed prior to deblocking and cleavage in liquid HF to avoid t-butylation of the methionine residue. The analogs were purified by chromatography on carboxymethylcellulose and partition chromatography on Sephadex G-50 and characterized where applicable by amino acid analysis, thin-layer chromatography, and paper electrophoresis.

The availability of these analogs which are very closely related chemically to $β_c$-endorphin afforded an opportunity to compare the various methods of purification and criteria of homogeneity. None could be distinguished from the parent molecule by carboxymethyl-cellulose chromatography, thin-layer chromatography and paper electrophoresis. On the other hand, three of the four proved to be readily separable from $β_c$-endorphin by partition chromatography and their $R_f$ values are shown in Table 1.

TABLE 1

Behavior of Analogs of $β_c$-Endorphin on Partition Chromatography in Sephadex G-50

| Peptide | $R_f$ |
| --- | --- |
| $β_c$-EP | 0.30 |
| [D-Tyr$^1$]-$β_c$-EP | 0.29 |
| [D-Ala$^2$]-$β_c$-EP | 0.35 |
| [D-Phe$^4$]-$β_c$-EP | 0.35 |
| [D-Met$^5$]-$β_c$-EP | 0.35 |

The opiate activities of the analogs relative to $β_c$-endorphin were measured in vitro in the guinea pig ileum (Brit. J. Pharmacol. 39, 398 (1970)) and in vivo by icv and iv injections using the tail-flick method (D'Amour and Smith, J. Pharmacol. Exp. Ther. 72,74 (1941). The results are summarized in Tables 2 and 3.

TABLE 2

Opiate Activity of Synthetic $β_c$-Endorphin Analogs by Guinea Pig Ileum Assay

| Preparations | IC$_{50}$ | Relative Potency |
| --- | --- | --- |
| $β_c$-Endorphin | $2.7 \times 10^{-8}$ | 100 |
| [D-Tyr$^1$9 -$β_c$-EP | $2.9 \times 10^{-6}$ | ≦1 |
| ]D-Ala$^2$]-$β_c$-EP | $6.3 \times 10^{-8}$ | 43 |
| [D-Phe$^4$]-$β_c$-EP | $6.7 \times 10^{-7}$ | 4 |
| [D-Met$^5$]-$β_c$-EP | $6.6 \times 10^{-7}$ | 4 |

TABLE 3

Analgesic Potency of Synthetic B$_c$-Endorphin and Analogs in Mice

| Preparation | AD$_{50}$* | Relative Potency |
| --- | --- | --- |
| Morphine sulfate | 0.42 (0.36–0.49) | 2.9 |
| $β_c$-endorphin | 0.11 (0.07–0.17) | 100.0 |
| [D-Tyr$^1$]-$β_c$-EP | 22.5 (13.4–37.8) | 0.5 |
| [D-Ala$^2$]-$β_c$-EP | 0.11 (0.08–0.17) | 100.0 |
| [D-Phe$^4$]-$β_c$-EP | >43 | <0.3 |
| [D-Met$^5$]-$β_c$-EP | 11.48 (7.17–18.36) | 1.0 |

*AD$_{50}$ in μg/25 g mouse (95% confidence limit)
The relative potencies are calculated on molar basis using the AD$_{50}$ of $β_c$-endorphin as 100%.

Among the synthetic analogs, [D-Ala$^2$]-β-endorphin was shown to possess the most significant analgesic activity and found to be equipotent to $β_c$-endorphin at doses of 0.11 to 0.42 μg injected icv; the D-Ala analog caused a dose-related increase in analgesic response with a duration of 30–90 min. and was blocked by naloxone. When a higher dose was given, the duration of response was prolonged and also blocked by naloxone. The analgesic potencies of [D-Met$^5$]- and [D-Try$^1$]-$β_c$-endorphin were 1.0 and 0.5%, respectively, of that for the parent molecule. [D-Phe$^4$]-$β_c$-endorphin was not active in inhibiting the tail-flick response at doses up to 43 μg; however, the animals showed hyperreactivity to touch or vocal stimulation.

β-endorphin is a potent analgesic after iv injection with an AD$_{50}$ of 9.4 mg/kg. [D-Ala$^2$]-$β_c$-endorphin at doses of 38.3 and 51.1 mg/kg injected iv inhibited the tail flick response for 10 to 20 min., but 25.5 mg/kg was not active. [D-Met$^5$] $β_c$-endorphin even at 120 mg/kg iv was not active in inhibiting the tail-flick response. It should be mentioned that the duration of action of β-endorphin is longer than its D-Ala² analog when given intravenously.

The enkephalin segment of β-endorphin contains three centers of asymmetry. Racemization during coupling of any of the D-amino acids involving these centers, or the presence of any L-isomer in the D-amino acids used, should give the highly active β-endorphin. The fact that [D-Phe⁴]- and [D-Met⁵]-$β_c$-endorphin were separable from $β_c$-endorphin in the purification steps strongly indicates that the biological activities measured for them are intrinsic. The case for [D-Try¹]-$β_c$-endorphin is not clear-cut, but the fact that its activities in the two assays do not stand in a 1:1 correspondence is supportive evidence that its activity is not entirely due to the presence of $β_c$-endorphin. All three analog exhibit decreases in biological activity which indicates the importance of the stereochemical relationships of the side-chain functions to each other in the enkephalin segment. However, it may be noted that [D-Met⁵]-$β_c$-endorphin still possesses analgesic activity inasmuch as $β_c$-endorphin itself is much more active than morphine in these assays.

The [D-Ala²]-$β_c$-endorphin possessed 100% analgesic potency compared with that of the parent molecule in in vivo assays (Table 3), however it possessed only 43% activity in in vitro assay (Table 2); the discrepancy between the in vivo and in vitro assay is not clear. There seems to be little correlation between these two assay systems in opioide peptides. These results are in sharp contrast to the greater analgesic activity of [D-Ala²]-β-enkephalinamide over that of enkephalin. The recent observations that $β_c$-endorphin is substantially more resistant to attack by leucine aminopeptidase than is enkephalin suggested that the former may already be quite stable to exopeptidases. Thus, the attempt to further stabilize the Tyr-Gly bond through the analog [D-Ala²]-$β_c$-endorphin led to little alteration in analgesic activity. However, as with enkephalin, the glycine in the 2-position of $β_c$-endorphin can be replaced by a D-amino acid without drastic reduction of biological activity. It should also be noted that the in vitro opioid activities of the other analogs are considerably higher than those obtained by the in vivo assay procedure (Tables 2 and 3).

The novel D-amino acid β-endorphin analogs of the present invention can be employed as opiate agonists and analgesic agents in a similar manner as their parent β-endorphin compounds. It is understood, of course, that their respective dosages will be adjusted for their relative potencies as shown by their in vivo bioactivity.

Sterile, stable solid dosage forms suitable for reconstitution for parenteral administration are obtained by filtering aqueous buffered solutions of the desired peptide through a sterilizing filter into sterile vials and then lyophilizing. The solid lyophilized product can be reconstituted at the time of use by the addition of sterile, isotonic saline. Other parenteral dosage forms known in the art for the administration of peptides can also be used.

The following examples serve to further illustrate the present invention. In such examples melting points were determined on a Fisher-Johns block and were uncorrected. All temperatures are in °C. Thin-layer chromatography (tlc) was run on silica gel in the following solvents: chloroform-acetic acid (15:1, v/v; CA); 1-butanol-acetic acid-water (4:1:1 v/v; BAW); 1-butanol-pyridine-acetic acid-water (5:5:1:4, v/v; BPAW); Chromatography on carboxymethylcellulose was performed at 24° in a 1.0×55-cm column with an initial buffer of 0.01 M NH₄OAc of pH 4.5 and collection of 10-ml fractions at a flow rate of ca 200 ml/hr. A gradient with respect to pH and salt concentration was effected through a 500-ml mixing chamber containing the starting buffer with 0.2 M NH₄OAc after fraction No. 10, and 0.4 M NH₄OAc after fraction No. 30. Partition chromatography on Sephadex G-50 was performed in a 1.76×46.5 cm column at 24° in the solvent system 1-butanol-pyridine-0.6 M NH₄OAc (5:3:10 v/v; pH of lower phase is 8.2) with collection of 2.98 ml fractions at about 8 ml/hr. Brominated chloromethyl styrene-1% divinyl benzene was prepared as described by Merrifield, J. Am. Chem. Soc. 85, 2149–2154 (1963) and Loffet, Int. J. Protein Res. 3, 297–299 (1971) with the exception that N-methylmorpholine replaced diisopropylethylamine used for the neutralization procedure.

EXAMPLE 1

O-Benzyloxycarbonyl-D-tyrosine

This compound was prepared from D-tyrosine (1.02 g) in the same manner as the L-isomer as described by Overell and Petrow, J. Chem. Soc. 232 (1955); yield, 0.73 g (40%); mp 208°–210° decn; tlc (BAW) $R_f$ 0.55; $[α]_D^{24}+9.1$ (c 2.14, 80% acetic acid).

Anal. Calcd for $C_{17}H_{17}NO_5$(315.325): C, 64.75; H, 5.43; N, 4.44. Found: C, 64.58; H, 5.48; N, 4.35.

EXAMPLE 2

$N^α$-t-Butyloxycarbonyl-O-(benzyloxycabonyl)-L-tyrosine

O-Benzyloxycarbonyl-L-tyrosine (8.6 g) was reacted with Boc azide (6.4 ml) in the presence of diisopropylethylamine (10.5 ml) in dimethylsulfoxide (180 ml). Work up by standard procedures for Boc-amino acids gave a product which was purified on a silica gel column by starting with CHCl₃ and eluting with increasing concentrations of ethyl acetate in CHCl₃. The desired product recovered from appopriate fractions was crystallized from ether-petroleum ether: yield, 7.0 g (62%); mp 85°–86°; tlc (CA) $R_f$ 0.6; $[α]_D^{24}+17.1°$ (c 4.1, absolute ethanol); $[α]_D^{24}+9.2°$ (c 4, methanol). Lit. (Semkin et al., 1968)* mp 152°; $[α]_D^{20}-7°$ (c 1, methanol).

Anal. Calcd. for $C_{22}H_{25}NO_7$(415.44): C, 63.61; H, 6.07; N, 3.37. Found: C, 63,83; H, 6.10; N, 3.40.

*Zh. Obshch. Khim. 38, 2358.

For determination of optical purity, a sample (412 mg) was treated in liquid HF (20 ml) in the presence of anisole (1.5 ml) for 30 min. at 0°. After removal of HF the residue was taken up in 1 N HCl (20 ml), washed with three 20-ml portions of ether, and evaporated to dryness. Quantitative amino acid analysis for tryosine gave a 97% yield. Determination of optical rotation gave $[α]_D^{24}-10.3°$ (c 3.6, 1 N HCl) based on the amount of tyrosine obtainable from the starting sample. The starting tyrosine had $[α]_D^{24}-10.2°$ (c 3.7, 1 N HCl).

EXAMPLE 3

$N^α$-t-Butyloxycarbonyl-O-(benzyloxycarbonyl)-D-tyrosine

This compound was prepared in the same manner as the L-isomer in Example 2 except that the silica gel chromatography step was omitted. Yield, 65%, mp 84°–85°; tlc (CA) $R_f$ 0.73; $[α]_D^{24}-17.9°$ (c 4.1, absolute ethanol).

Anal. Calcd for $C_{22}H_{25}NO_7$(415.44): C, 63.61; H, 6.07; N, 3.37. Found: C, 63.82; H, 6.04; N, 3.45.

EXAMPLE 4

Protected $\beta_c$-endorphin-(6-31) Polymer

The tetramethyl ammonium salt of Boc-glutamine (7.8 mmol) was reacted at 24° with 4.4 g of brominated polymer in DMF (30 ml) in the presence of KI (51 mg) for 42.5 hr. The resin was worked up as described previously by Yamashiro and Li, J. Am. Chem. Soc., 95, 1310 (1973). Removal of the Boc group and amine determination indicated a load of 0.49 mmol per g. Synthesis of the sequence corresponding to $\beta_c$-endorphin-(6-31) was started with 2.45 g of the Boc-Gln-bromopolymer (1.21 mmol) and performed manually. The schedules for synthesis followed the same tactics described for the synthesis of $\beta_c$-endorphin as described in U.S. Patent Application Ser. No. 667,747, filed March 17, 1976. Side chain protecting groups were: Lys, 2-BrZ; His, Z; Thr, 4-chlorobenzyl; Ser, 4-bromobenzyl; Glu, 4-bromobenzyl. Yield of protected peptide resin was 8.25 g (99.5% of theoretical weight gain).

EXAMPLE 5

Synthesis of the sequence corresponding to $\beta_h$-endorphin (6-31) is carried out using the tactics described in the aforesaid U.S. Patent Application Ser. No. 667,747. The desired protected peptide resin is obtained in good yield and purity.

EXAMPLE 6

Synthesis of Analogs

A sample of the peptide resin prepared in Example 4 (340 mg) corresponding to an original load of 50 μmol was used for synthesis of each of the analogs as well as $\beta_c$-endorphin as control. Side-chain protection of D- and L-tyrosine was Z since it was deemed unnecessary to have an acid stable protecting group. The Boc derivatives of D-alanine, D-phenylalanine and D-methionine were used. The Boc group of the final protected peptide resin was removed before proceeding to treatment with liquid HF (ca. 5 ml, 75 min. at 0°) in the presence of anisole (0.5 ml). After removal of HF with a stream of nitrogen ($<0°$) the residue was washed with ethyl acetate (25 ml) and the product extracted with 0.5 N acetic acid (5 ml). Purification was effected by gel filtration in a 2.16×25-cm column of Sephadex G-10 in 0.5 N acetic acid (3 ml fractions), chromatography on carboxymethylcellulose, and partition chromatography on Sephadex G-50. Overall yields based on starting Boc-Gln-bromopolymer (50 μmol) and on peptide content by amino acid analysis: $\beta_c$-endorphin, 48 mg (23%); [D-Tyr$^1$]-$\beta_c$-endorphin, 43 mg (20%); [D-Ala$^2$]-$\beta_c$-endorphin, 46 mg (25%); [D-Phe$^4$]-$\beta_c$-endorphin, 46 mg (27%), and [D-Met$^5$]-$\beta_c$-endorphin, 64 mg (35%).

Amino acid analyses of acid hydrolysates are given in Table 4.

TABLE 4

| Amino Acid Analyses of $\beta_c$-Endorphin and Analogs[a] | | | | | |
|---|---|---|---|---|---|
| Amino Acid | $\beta_c$-EP | [D-Tyr$^1$]-$\beta_c$-EP | [D-Ala$^2$]-$\beta_c$-EP | [D-Phe$^4$]-$\beta_c$-EP | [D-Met$^5$]-$\beta_c$-EP |
| Lys | 5.1 | 5.2 | 5.0 | 5.0 | 5.2 |
| His | 1.0 | 1.0 | 1.0 | 1.0 | 1.1 |
| Asp | 2.0 | 2.0 | 2.0 | 2.1 | 2.0 |
| Thr | 2.9 | 2.9 | 2.8 | 2.9 | 2.9 |
| Ser | 1.8 | 1.8 | 1.7 | 1.8 | 1.8 |
| Gln | 3.2 | 3.2 | 2.9 | 3.0 | 3.0 |
| Pro | 1.0 | 0.9 | 1.1 | 1.1 | 0.9 |
| Gly | 2.9 | 2.8 | 2.1 | 2.8 | 2.9 |
| Ala | 2.0 | 2.0 | 3.2 | 2.2 | 2.2 |
| Val | 1.0 | 1.0 | 0.9 | 1.0 | 1.0 |
| Met | 1.0 | 0.9 | 0.9 | 1.0 | 1.0 |
| Ile[b] | 1.7 | 1.8 | 1.7 | 1.6 | 1.6 |
| Leu | 2.0 | 2.0 | 2.0 | 1.9 | 1.9 |
| Tyr | 1.0 | 1.0 | 0.9 | 0.9 | 0.9 |
| Phe | 2.0 | 2.0 | 2.0 | 1.9 | 1.9 |

[a]Hydrolysis in constant boiling HCl at 110° for 24 hr.
[b]Values taken from a 72-hr hydrolysis relative to leucine.

Thin-layer chromatography (BPAW) gave a single spot (detection by ninhydrin and chlorine-tolidine) for each peptide with identical $R_f$ values (0.48). The $\beta$-endorphins tend to form an impenetrable coat on spotting and drying for tlc, therefore solutions of high concentrations (25 mg/ml) were prepared so that spotting could be accomplished with a single application. Paper electrophoresis on Whatman 3 MM (400 V, 4 hr) gave a single spot (ninhydrin detection) for each peptide at pH 3.7 (pyridine acetate buffer) with idential $R_f$ values (0.65 relative to lysine) and at pH 6.7 (collidine acetate buffer), also with identical $R_f$ values (0.50 relative to lysine).

Analytical partition chromatography on Sephadex G-50 was performed in a 1.18×59.8 cm column. Equilibration of the column with the upper phase was performed with 4 hold-up volumes before starting the first sample application. Samples (4 mg) of $\beta_c$-endorphin and each of the analogs were run with collection of 0.895-ml fractions at a flow rate of 4.5 ml/hr at 24°. Each gave a single symmetrical peak (detection by Folin-Lowry analysis) with $R_f$ values indicated in Table 1. The sharpness of each peak was substantially greater than in the preparative runs.

EXAMPLE 7

The protected peptide of Example 5 is treated with $N^\alpha$-t-butyloxycarbonylO-(benzyloxycarbonyl)-D-tyrosine, Boc-D-alanine, Boc-D-phenylalanine and Boc-D-methionine in analogy to the procedures described above in Example 6 to provide correspondingly [D-Tyr$^1$]-$\beta_h$-endorphin, [D-Ala$^2$]-$\beta_h$-endorphin, [D-Phe$^4$]-$\beta_h$-endorphin and [D-Met$^5$]-$\beta_h$-endorphin each in good yield and purity. These compounds exhibit the same order of activity in the guinea pig ileum assay and the mouse tail flick method as the corresponding camel endorphin analogs.

EXAMPLE 8

The opiate activity was assayed in vitro by electrically stimulated myenteric plexus longitudinal muscle preparation from guinea pig ileum by the method of Kosterlitz et al., supra.

The analgesic properties of $\beta$-endorphin and its analogs were also assessed in mice by the tail-flick method of D'Amour and Smith, supra. The peptides, dissolved in saline, were injected either icv in a volume of 5 μl, according to the method described by Haley and McCormick, Brit. J. Pharmacol. 12, 12 (1957) or iv via the tail vein. To evaluate this analgesic response, a control latency ($T_0$) was obtained from the mean of two latencies determined prior to drug injections, and the test latencies ($T_1$) were determined at various times after injection for each animal. "Percent analgesic" was calculated as $[(T_1-T_0)/(T_2-T_1)]\times 100$, where the cut off time ($T_2$) was 10 sec. Results are summarized in Tables 2 and 3 above.

I claim:
1. A [D-Ala$^2$]$\beta$-endorphin analog.
2. The analog of claim 1 wherein said $\beta$-endorphin is $\beta_c$endorphin.
3. The analog of claim 1 wherein said $\beta$-endorphin is $\beta_h$-endorphin.

* * * * *